United States Patent [19]

Butler et al.

[11] Patent Number: 4,774,379

[45] Date of Patent: Sep. 27, 1988

[54] AROMATIC ALKYLATION PROCESS

[75] Inventors: James R. Butler; Kevin P. Menard; J. Randall Curtis, all of Big Spring, Tex.

[73] Assignee: Cosden Technology, Inc., Dallas, Tex.

[21] Appl. No.: 60,110

[22] Filed: Jun. 9, 1987

[51] Int. Cl.$^4$ .............................................. C07C 2/68
[52] U.S. Cl. ................................................... 585/467
[58] Field of Search ....................................... 585/467

[56] References Cited

U.S. PATENT DOCUMENTS

| Re. 29,948 | 3/1979 | Dwyer et al. | 208/110 |
|---|---|---|---|
| 3,702,886 | 11/1972 | Arqauer et al. | 423/328 |
| 4,061,724 | 12/1977 | Grose et al. | 423/335 |
| 4,104,319 | 8/1978 | Kaeding | 585/454 |
| 4,139,600 | 2/1979 | Rollmann et al. | 423/329 |
| 4,309,276 | 1/1982 | Miller | 208/109 |
| 4,387,260 | 6/1983 | Watson et al. | 585/467 |
| 4,441,991 | 4/1984 | Dwyer et al. | 208/111 |
| 4,489,214 | 12/1984 | Butler et al. | 585/467 |
| 4,490,570 | 12/1984 | Forward et al. | 585/467 |
| 4,520,220 | 5/1985 | Watson et al. | 585/467 |
| 4,587,371 | 5/1986 | Forward et al. | 585/467 |
| 4,599,473 | 7/1986 | Debras et al. | 585/415 |

OTHER PUBLICATIONS

Debras et al., "Physico-Chemical Characterization of Pentasil Type Materials, I. Precursors and Calcined Zeolites, and II., Thermal Analysis of the Precursors," *Zeolites*, 1985, vol. 5, pp. 369-383.

*Primary Examiner*—Curtis R. Davis
*Attorney, Agent, or Firm*—William D. Jackson; Mark A. Montgomery; John K. Abokhair

[57] ABSTRACT

A process for the alkylation of aromatic compounds employing silicalite of extremely low sodium content. A feedstock containing an aromatic substrate such as benzene is supplied along with an alkylating agent such as ethylene to a reaction zone containing a silicalite alkylation catalyst having a sodium content of less than 100 ppm Na$_2$O. Steam may be cofed to the reaction zone in an amount of at least 1 wt. % based upon the aromatic substrate. The low sodium silicalite has a substantially better aging quality in the alkylation process than does silicalite which normally has a higher sodium content.

11 Claims, 3 Drawing Sheets

AROMATIC ALKYLATION PROCESS

BACKGROUND ART

The use of molecular sieves as catalysts in the alkylation of aromatic feedstocks is well known in the art. Two molecular sieve catalysts which may be employed in such alkylation processes are ZSM-5 and silicalite. ZSM-5 zeolites and methods for their preparation are disclosed in U.S. Pat. No. 3,702,886 to Argauer et al and U.S. Pat. No. 3,941,877 (Re 29,948) to Dwyer et al. Silicalite and its preparation are disclosed in U.S. Pat. No. 4,061,724 to Grose et al.

Both silicalite and ZSM-5 type catalysts can be characterized very generally in terms of mole oxide ratios as follows:

Wherein:
M is an alkali metal cation, normally sodium
x is the mole ratio of alkali metal oxide to alumina, and
y is the silica/alumina ratio.

For the traditional ZSM-5 zeolite, y ranges from about 5 to about 100 although in the case of highly siliceous ZSM-5 zeolites of the type disclosed in Dwyer, termed metal organosilicates, y can be substantially greater than 200. x is about 1, resulting in an $Na_2O$ content in the molecular sieve structure which is normally above 1 wt. % although in the case of the organometal silicates of Dwyer, the $Na_2O$ content can be substantially less. In the case of silicalite, y is normally greater than 200, typically about 300, although it may be substantially greater, and x is usually substantially less than 1. Expressed in terms of wt. % of the molecular sieve structure, the $Na_2O$ content is usually less than that of ZSM-5 and normally less than 1 wt. % in any event.

It has been proposed in various prior art processes involving either ZSM-5 zeolites or silicalite to adjust the sodium content of the catalyst. Thus U.S. Pat. No. 4,441,991 to Dwyer et al directed to hydrodewaxing over a highly siliceous porous crystalline catalyst "related to" the zeolite ZSM-5, and having a silica/alumina ratio greater than 200, discloses that it is preferred to reduce the sodium or other alkali metal content of the as synthesized zeolite to a value of less than 50% of the original sodium content. By thus reducing the sodium content, the product as used will have a sodium concentration of less than 0.5 wt. % and usually less than 0.1. Dwyer goes on to state that the sodium content is preferably less than 0.03% and most preferably less than about 0.01%. While the Dwyer disclosure is principally directed to crystalline materials prepared in accordance with Dwyer Re 29,948, the patent also refers to silicalite as a catalyst "related to" the zeolite ZSM-5.

U.S. Pat. No. 4,309,276 to Miller discloses the use of silicalite in a hydrocarbon conversion process involving the production of olefins from a paraffinic feed. Miller discloses that the sodium content of the silicalite should be less than 0.1 wt.% and most preferably less than about 0.01 wt.%. Specifically disclosed are silicalites having sodium contents of 140 and 400 ppm, corresponding to 189 and 539 ppm, $Na_2O$, respectively.

As noted previously, both ZSM-5 type zeolites and silicalite are known in the art as catalysts for use in the alkylation of aromatic substrates. U.S. Pat. No. 4,387,260 to Watson et al discloses the alkylation of aromatic compounds such as benzene or toluene over silicalite in which a water cofeed is employed to prolong the cycle length of the process between catalyst regenerations. The water cofeed is supplied in an amount preferably within the range of 20,000–100,000 ppm based upon the aromatic substrate and more preferably within the range of 20,000–60,000 ppm. Silicalite is also effective in the production of ortho-suppressed and para-enhanced dialkyl aromatic compounds as disclosed in U.S. Pat. Nos. 4,489,214 (Butler et al) and 4,490,570 (Forward et al). It is also an effective catalyst in the production of alkyl aromatic compounds such as ethyl benzene where sulfur is present in the feedstock either as a contaminant in the ethylene stream or in the benzene stream, as disclosed in U.S. Pat. No. 4,587,371 to Forward et al.

The aforementioned patents do not address the subject of the sodium content of the silicalite catalysts. Where ZSM-5 type zeolites have been used in the alkylation of aromatic compounds it has been proposed to use ZSM-5 zeolites of moderately low sodium content. For example, U.S. Pat. No. 4,139,600 to Rollmann et al discloses the synthesis of low sodium ZSM-5 crystalline aluminosilicalites said to be useful in processes including the alkylation of aromatics with olefins. Exemplary materials given in the Rollman patent characterized as being "very low" in sodium had less than 0.4% sodium. In terms of the amount relative to aluminum, the $Na_2O/Al_2O_3$ ratio of the ZSM-5 products was below 0.25. U.S. Pat. No. 4,104,319 to Kaeding discloses the ethylation of a monoalkyl benzene with two ZSM-5 catalysts. One of a moderately high silica/alumina ratio of 70/1, had a sodium content of 0.05 wt.%. The other, having an extremely high silica/alumina ratio of 1670 also had a substantially higher sodium content of 1.6 wt.%.

SUMMARY OF THE INVENTION

In accordance with the present invention there is provided a new and improved process for the alkylation of aromatic compounds in which a silicalite catalyst of ultra low sodium content is employed. The ultra low sodium silicalite exhibits substantially better aging qualities than the more conventional silicalite of somewhat higher sodium content.

In carrying out the invention a feedstock containing an aromatic substrate is supplied to a reaction zone and brought into contact with a shape selective crystalline silica polymorph silicalite catalyst within the reaction zone. The silicalite alkylation catalyst has a sodium content of less than 100 wt. ppm expressed as $Na_2O$. An alkylating agent is also supplied to the reaction zone which is operated at temperature and pressure conditions to effect alkylation of the aromatic substrate by the alkylating agent. The resulting alkylated aromatic product is recovered from the reaction zone.

Preferably water is cofed to the reaction zone in an amount of at least 1 wt. % based upon the alkylatable aromatic substrate. The sodium content of the silicalite catalyst preferably is no more than 50 wt. ppm $Na_2O$ and, more desirably, no more than 30 ppm $Na_2O$. One suitable way of arriving at the desired low sodium content is by washing the silicalite catalyst with an ammonium solution such as an aqueous ammonium salt solution or an aqueous ammonium hydroxide solution adjusted to be neutral or near neutral, e.g., a pH of about 6–8. This washing technique enables the sodium content of the silicalite catalyst to be reduced to a value no greater than 20 ppm $Na_2O$.

BEST MODES OF THE INVENTION

Figure 1:
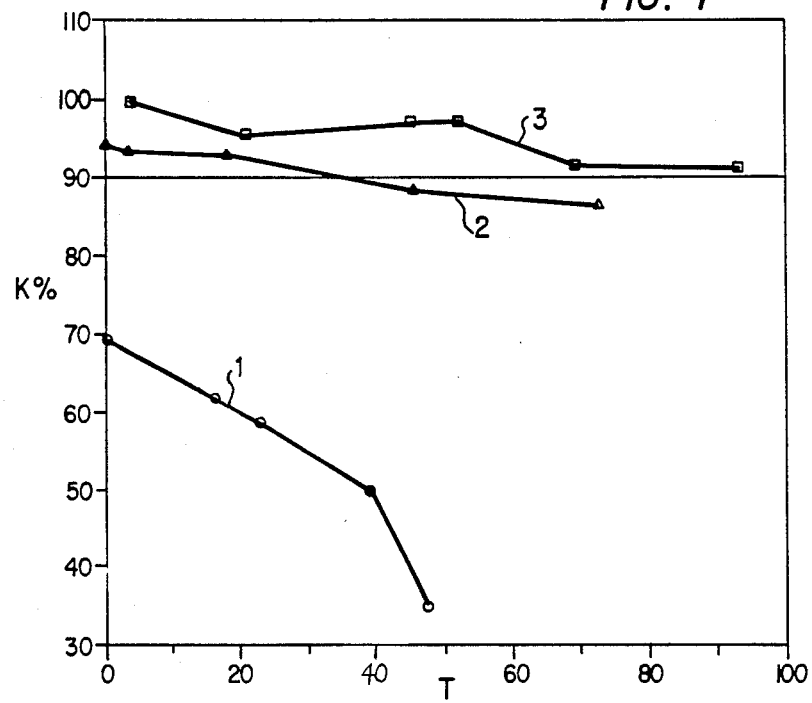
FIGS. 1-5 are graphs illustrating the results of experimental work relative to the present invention carried out employing silicalite catalysts of differing sodium content.

As noted previously, silicalite is a highly effective catalyst for the alkylation of aromatic hydrocarbons. The present invention employing a silicalite catalyst of extremely low sodium content may be carried out in a manner to implement the various alkylation procedures known in the art. Preferably, the alkylation procedure will be carried out with a water cofeed as disclosed in the aforementioned U.S. Pat. No. 4,387,260 to Watson et al. However the procedure may be carried out in the absence of a steam cofeed as disclosed in U.S. Pat. No. 4,520,220 to Watson et al. In either case, the present invention may be carried out in accordance with the process parameters and procedures described in these two patents. Thus the reaction zone pressure may vary from atmospheric up to about 35 bars and normally will fall within the range of 14–24 bars. The reaction zone normally will be operated at a temperature within the range of 340°–600° C. and preferably within the range of 380°–430° C. The alkylation reaction is exothermic resulting in a positive temperature differential from the reactor inlet to the reactor outlet of about 20°–100° C. Where reference is made to reaction temperature herein, the temperature referred to is the inlet temperature to the reactor or where several reactors are used, the average inlet temperature.

The mole ratio of alkylating agent to the alkylatable aromatic substrate may be varied in accordance with the desired reaction product. Normally a substantial stoichiometric excess of aromatic compound relative to the alkylating agent will be employed. For example, to where ethylene is employed in the alkylation of toluene or benzene to produce ethyl toluene or ethyl benzene, the mole ratio of the alkylatable substrate to ethylene should be within the range of 20-3. In any case, there should be a substantial stoichiometric excess of the alkylatable substrate. The space velocity based upon the alkylatable substrate normally will be within the range of 30–200 hours$^{-1}$. Where steam cofeed is supplied, it normally will be added in an amount of at least 1 wt. % based upon the aromatic substrate. The alkylation procedure may be carried out in one reaction zone or in a series of reaction zones. In the latter case, the alkylated product from one reaction zone can be fed to a subsequent reaction zone along with additional alkylating agent. For a further description of the process parameters and procedures which may be employed in the alkylation of aromatic compounds in accordance with the present invention, reference is made to the aforementioned U.S. Pat. Nos. 4,387,260 and 4,520,220, the entire disclosures of which are incorporated herein by reference.

The invention is believed to have particular applicability in regard to the alkylation of unsubstituted aromatic compounds to produce monoalkylated aromatic compounds e.g. the ethylation of benzene by ethylene to produce ethyl benzene. However, it may also be employed in the alkylation of alkyl substituted aromatic compounds as disclosed in the aforementioned U.S. Pat. Nos. 4,489,214 (Butler et al) and 4,490,570 (Forward et al).

While silicalite is normally of orthorhombic symmetry as disclosed in the aforementioned patent to Grose et al., it may be converted to monoclinic symmetry to enhance para selective alkylation of monoalkyl benzenes. For a further description of the conversion of silicalite from orthorhombic to monoclinic symmetry and its use in the paraselective alkylation of aromatic hydrocarbons, reference is made to U.S. Pat. No. 4,599,473 to Debras et al. The silicalite employed in the present invention may be either orthorhombic or monoclinic and it need not be modified except for pretreatment as described hereinafter to arrive at the requisite ultra low sodium content.

The silicalite catalyst employed in the present invention has a sodium content of less than 100 ppm $Na_2O$. Preferably, the sodium content is no more than 50 ppm. Silicalite can be synthesized to provide this low sodium content but it is believed that in some cases silicalite, even when originally of the requisite low sodium content, may have sodium inadvertently introduced into the molecular sieve structure when mixed with a binder in the course of a normal pelletizing procedure. Thus, even though the silicalite is originally of the desired low sodium content, it may be necessary to subject the final extruded product to an extraction procedure to ensure that the sodium content is reduced to the desired low level. As indicated by the experimental work hereinafter, the lower the sodium content the better, in terms of aging quality. Sodium levels of less than 30 ppm or the most desirable level of ≦20 ppm $Na_2O$ can be achieved economically in accordance with the present invention by simple extraction techniques.

A suitable extraction technique involves washing with an aqueous ammonium salt solution since this readily achieves the very low sodium content desirable for this invention. The washing techniques using aqueous solutions of sodium chloride or hydrochloric acid disclosed in the aforementioned patent to Grose et al apparently do not provide the requisite low sodium content in the silicalite. In fact, washing with sodium chloride may introduce sodium into the molecular sieve structure. Grose discloses that washing of silicalite having an original alkali metal content expressed as $Na_2O$ of slightly in excess of 1 wt. % was reduced to about 0.09% after washing with one normal HCl for one hour at 20° C. Even when washing with the hydrochloric acid solution or a 5 molar sodium chloride solution at elevated temperatures of 80°–100° C., the alkali metal content was reduced to <0.02 wt. %, equivalent to about 200 ppm $Na_2O$ which is well above the levels contemplated in this invention.

Silicalite may be contrasted with the ZSM-5 zeolites which are characterized as aluminosilicates as disclosed in U.S. Pat. No. 3,702,886 to Argauer et al or, in the case of high silica/alumina ratio (essentially aluminum-free) ZSM-5 type zeolites, as metal organosilicates as disclosed in Re 29,948 (U.S. Pat. No. 3,941,871) to Dwyer et al. As noted above, silicalite is disclosed in U.S. Pat. No. 4,061,724 to Grose et al and for further description of silicalite and its method of preparation the entire disclosure of the Grose et al patent is incorporated herein by reference. Minor amounts of aluminum, which normally will be found as an impurity in silica sources, will be present in silicalite. However, the aluminum content of silicalite is less than 1 aluminum atom for each unit cell of 96 SiO$_2$ tetrahedra. Thus, silicalite has a silica/alumino ratio of about 200 or more.

Similarities and differences between silicalite and ZSM-5 type zeolites are examined in Debras et al "Physico-chemical characterization of pentasil type materials, I. Precursors and calcined zeolites, and II. Thermal analysis of the precursors," Zeolites, 1985, Vol. 5, pp. 369-383. As explained in Debras, the ZSM-5 materials were synthesized following the teachings of the aforementioned Argauer et al patent (termed in the paper the "A" procedure) and the silicalite materials were synthesized following the teachings of the Grose et al patent (the "G" procedure).

As disclosed in Debras part I, the synthesis procedures used in the preparation of the silicalite "G" materials and the ZSM-5 zeolite "A" materials are different in several respects. The ratio of silica to the quaternary ammonium templating agent used to produce the "A" materials is much lower than the corresponding ratio used to produce the G materials. In addition, the H$_2$O/SiO$_2$ ratio for the "A" materials is substantially higher than the H$_2$O/SiO$_2$ ratio for the "G" materials.

Insofar as the materials themselves are concerned, the Debras et al paper reports several significant differences. The average crystal size of silicalite at less than 1 aluminum atom per unit cell is greater than the average crystal size for ZSM-5 zeolite (the "A" material). Silicalite has an average crystal size greater than 5 microns. As disclosed in Debras et al at an aluminum/unit-cell ratio of less than 1, silicalite has an average crystal size of about 10 microns or more, whereas for ZSM-5 zeolites, the average crystal size is about 2 microns. The crystal sizes of the two materials are shown in FIGS. 3a and 3b of Part I of Debras et al. As further disclosed in the Debras et al paper, ZSM-5 crystals have an aluminum rich core surrounded by an aluminum deficient outer shell. For the silicalite materials on the other hand, the core is aluminum deficient compared with the outer shell. That is, the aluminum gradient for silicalite is exactly opposite that of ZSM-5 zeolite. The aluminum gradients of the silicalite and ZSM-5 materials are shown in Table 3 and FIG. 5 of Debras et al, Part I.

It is a conventional practice to promote ZSM-5 type zeolite catalysts with metals such as nickel and platinum. Various other metals which may be used to promote or modify zeolite catalysts include zinc, palladium, calcium, copper, manganese, magnesium, and other metals such as disclosed in the aforementioned patents to Rollmann and Kaeding. Metal oxides or sulfides may also be used. The silicalite catalyst employed in the present invention can be unmodified; that is, the catalyst need not be promoted to incorporate the various metal agents which are commonly employed in the ZSM-type zeolites, In the experimental work reported herein, unmodified catalyst was used.

In experimental work relative to the invention benzene was alkylated with ethylene over silicalite catalysts of varying sodium content. The silicalite catalysts had silica/alumina mol ratios of about 300-320 and had sodium contents ranging from less than 20 to more than 200 ppm Na$_2$O, as will appear hereinafter. The aforementioned parameters are with respect to the silicalite itself and do not take into account the alumina binder which was used to formulate the catalyst particles for the test. The catalyst particles were in the form of extrudates having an average diameter of about 1/16 inch. The binder comprised about 15 to 20% of the catalyst particles, the remainder being the silicalite.

In the laboratory work described below, the inlet temperature to the reactor ranged from about 380°-440° C. and was usually about 400° to 420° C. The exotherm across the reactor resulted in a positive temperature gradient from the inlet to the outlet of about 20°-40° C. The average pressure for all runs was about 300 psig. Steam cofeed was supplied to the reactor in an amount of 1 wt. % of the benzene. The molar ratio of benzene to ethylene ranged from about 7 to 9 and the space velocity (WHSV) of the benzene feed was about 75-95 hours$^{-1}$ and usually about 80-90 hours$^{-1}$. The relatively small variations in the experimental conditions from one test to another are not thought to significantly affect the comparative experimental results.

All of the experimental work was carried out with silicalite of very low sodium content. As shown by the experimental work reported below, even small amounts of sodium indicated in the prior art to be acceptable or even preferred for various conversion processes adversely affected the aging quality of silicalite used as a catalyst in aromatic alkylation. This is reflected by experimental work carried out employing silicalite having a sodium content of 224 ppm Na$_2$O or less. This is well below the sodium content of silicalite indicated as being acceptable or even preferred in hydrocracking type conversion reactions as disclosed in the aforementioned patent to Miller and also much less than the level of sodium in low sodium ZSM-5 zeolites employed in alkylation reactions as disclosed in the aforementioned patents to Kaeding and Rollmann.

In one set of experimental work ethylation of benzene was carried out employing silicalite catalysts having sodium contents of 224 ppm, 135 ppm, 65 ppm, and 54 ppm Na$_2$O. An additional run was carried out employing a silicalite catalyst sample derived by washing silicalite originally having a sodium content of 224 ppm Na$_2$O with an ammonium ion solution to reduce the sodium content of the silicalite to 13 ppm Na$_2$O. The analyses of the silicalite catalyst in the extruded form including the binder are set forth in Table I. The catalysts are identified as Catalyst A (Na$_2$O content of 224 ppm), Catalyst B (135 ppm) Catalyst C (65 ppm), Catalyst D (54 ppm) and Catalyst A-A (13 ppm).

TABLE 1

| Item | A | B | C | D | AA |
|---|---|---|---|---|---|
| % SiO$_2$ | 80.7 | 81.1 | 80.9 | 80.4 | 80.9 |
| % Al$_2$O$_3$ | 19.1 | 19.3 | 20.3 | 20.1 | 19.3 |
| % C | <0.02 | 0.02 | <0.02 | <0.02 | — |
| % NO$_3$ | <0.01 | 0.01 | <0.01 | <0.01 | <0.01 |
| Na$_2$O, PPM | 224 | 135 | 65 | 54 | <13 |
| K$_2$O, PPM | 561 | 258 | 605 | 599 | 73 |
| TiO$_2$, PPM | 599 | 517 | 619 | 601 | 506 |
| P$_2$O$_5$, PPM | <52 | 45 | <53 | <51 | 45 |
| MgO, PPM | 632 | 601 | 634 | 616 | 618 |
| % Fe$_2$O$_3$ | 0.1 | 0.09 | 0.110 | 0.107 | 0.150 |
| CaO, PPM | 630 | 336 | 616 | 598 | 473 |
| ZrO$_2$, PPM | 88 | 84 | 88 | 89 | 89 |

The results of three runs employing samples of Catalyst A are illustrated in FIG. 1. FIG. 1 is a graph of the percent conversion K (mols of ethylbenzene in the product as a percent of mols of ethylene in the feed) on the ordinate plotted as a function of the cumulative run time of the run (Catalyst age) T in hours plotted on the abscissa. In FIG. 1 Curve 1 shows the results of the catalyst sample which was first heat treated at about 760° C. for 16 hours before being placed in the laboratory reactor. Curve 2 shows the results for a catalyst sample which was loaded directly into the reactor without prior heat treatment. Both of the catalyst samples used in Runs 1 and 2 were from catalysts which had been previously used in alkylation procedures and then regenerated. A third run for Catalyst A was carried out with a sample of fresh catalyst,. i.e., one that had not been previously regenerated. The results of this run are shown by curve 3 in FIG. 1.

In the experimental work presented in FIG. 1, the catalyst employed in Run 1 was initially unacceptable and deteriorated rapidly after only a few days of testing. It is believed that this low activity of the catalyst was due to the relatively severe heat treatment process which may have caused damage to the catalyst structure. The catalysts employed in Runs 2 and 3 performed considerably better; however, both of these catalyst exhibited relatively rapid deactivation. In Run 2, the catalyst exhibited an incremental reduction in activity of 5% after 50 hours. The catalyst employed in Run 3 showed a similar loss in conversion activity after 60 hours.

Figure 2:
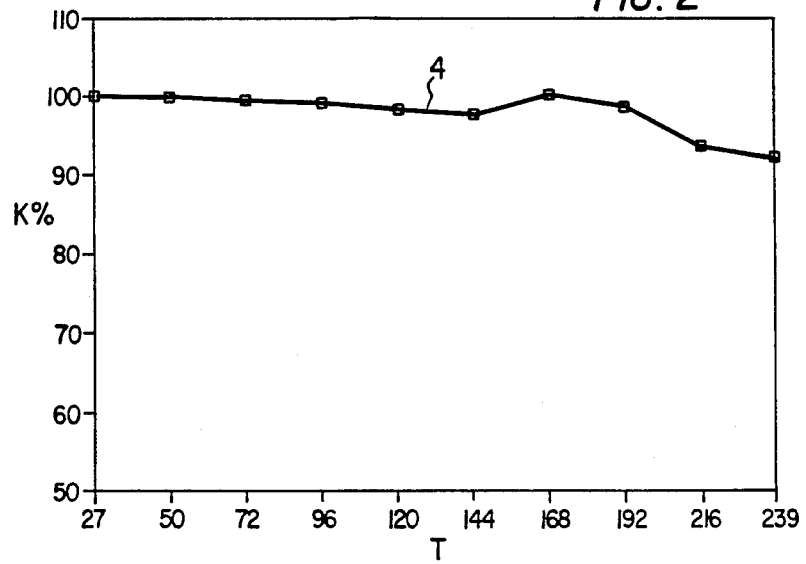

FIG. 2 shows the results achieved in a test carried out on a sample of Catalyst B having a sodium content of 135 ppm $Na_2O$. As shown by curve 4, the aging quality of this catalyst was improved significantly relative to the aging quality of the catalyst having the higher sodium content. Here, the catalyt showed an incremental 5% loss of conversion activity after about 200 hours. The increase in activity observed at 168 and 192 hours is thought to be the result of experimental error and not indicative of a real increase in catalyst activity.

Figure 3:
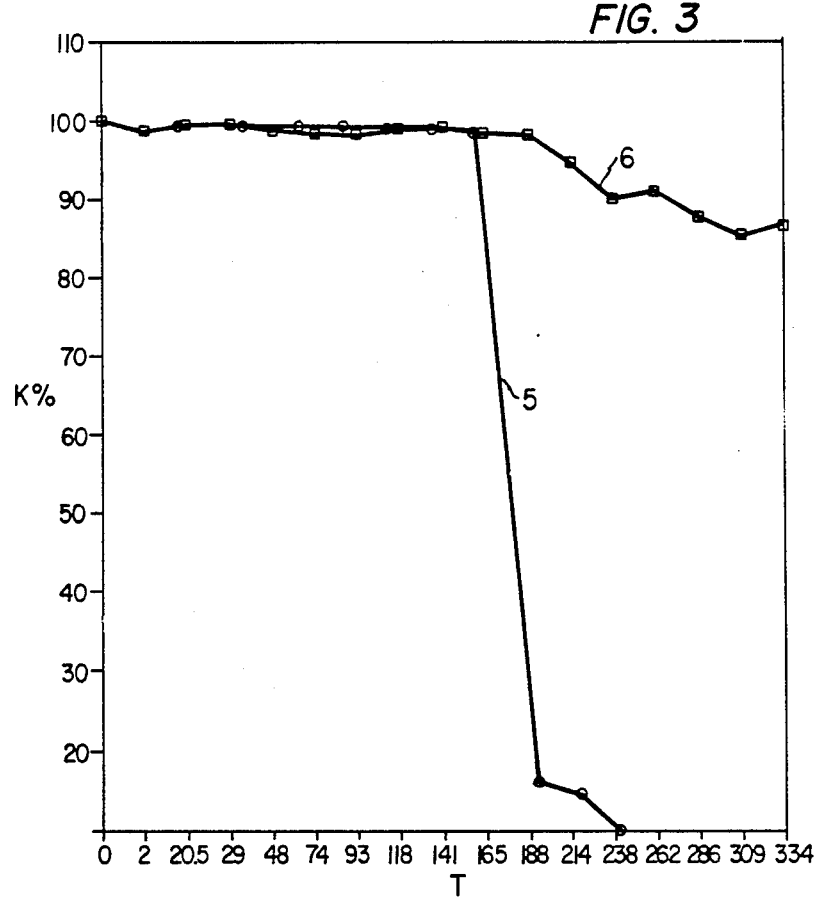

Curves 5 and 6 in FIG. 3 illustrate the results of benzene ethylation carried out employing samples from Catalysts C (65 ppm $Na_2O$) and D (54 ppm $Na_2O$), respectively. Both of these catalysts showed practically no loss in activity the first 7 to 8 days of testing. As illustrated by curve 6, the sample from Catalyst D had practically no loss in the conversion activity for the first 190 hours. The activity then declined rapidly resulting in an incremental loss of 5% conversion after about 200 hours. Catalyst C of slightly higher sodium content showed almost identical results until the conversion activity declined drastically during the eighth day of testing. It is believed that the sharp loss of activity indicated by curve 5 and the less drastic but still uncharacteristic behavior indicated by curve 6 are the results of experimental error or faulty experimental procedure. The earlier portions of curves 5 and 6 are believed to be more representative of the true characteristics of the catalyst.

Figure 4:
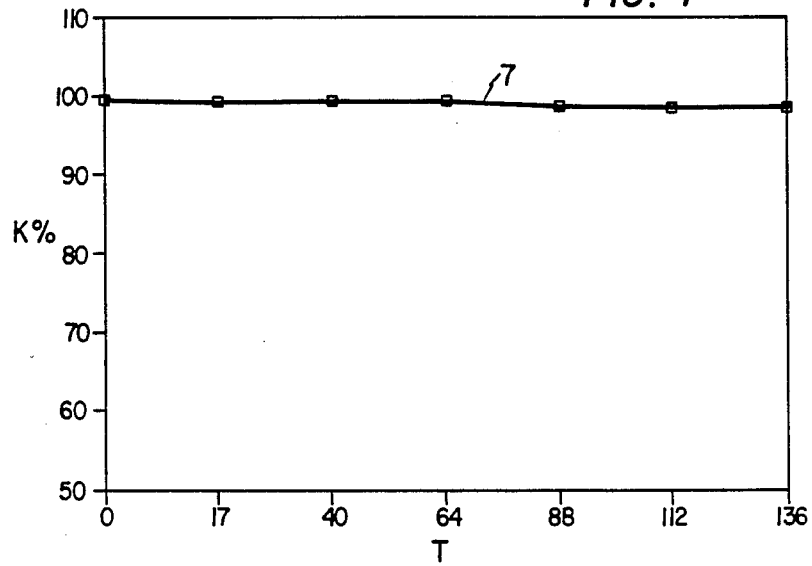

FIG. 4 indicates results of benzene ethylation carried out over a sample of Catalyst A—A. This sample was obtained from a fresh catalyst having an initial $Na_2O$ content of 224 which was washed in a ammonium ion solution to reduce the sodium content to 13 ppm $Na_2O$. As illustrated by curve 7, the conversion rate remained essentially flat throughout the test run. When the test was terminated at about 140 hours the catalyst exhibited a high activity of 98% conversion. The results as shown by curve 7 of FIG. 4 can best be compared with curve 2 of FIG. 1 to illustrate the substantially better results achieved by reducing the sodium content of the catalyst.

Additional experimental work was carried out with a silicalite Catalyst E having a sodium content of 92 ppm $Na_2O$, and a Catalyst EA obtained by washing Catalyst E with an ammonium solution to produce a catalyst having a $Na_2O$ content of about 50 ppm.

Figure 5:
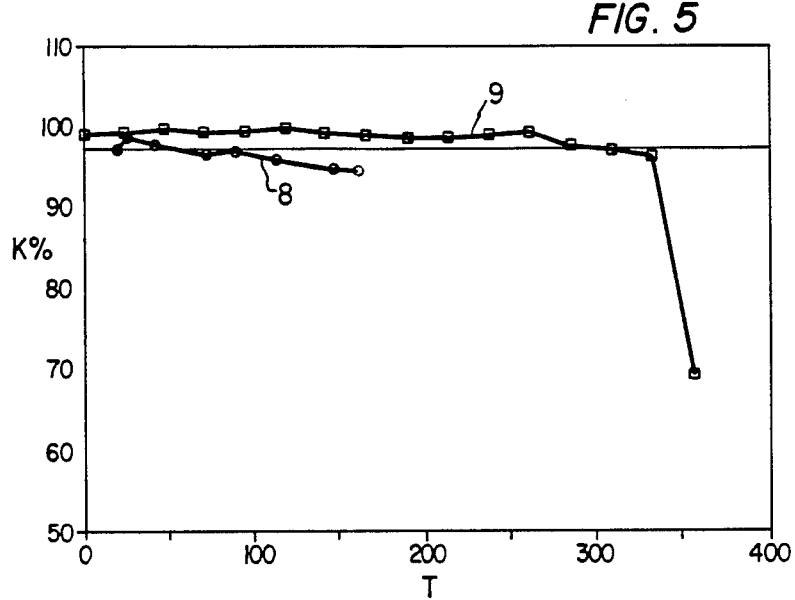

The results of experimental runs carried out employing samples of Catalysts E and EA, in terms of % conversion, K, time, T, in hours, are set forth in FIG. 5. Curve 8 in FIG. 5 shows the conversion activity of the catalyst with time for a sample of Catalyst E having a $Na_2O$ content of 92 ppm. Curve 9 shows the results from a run employing a sample of the ammonium washed Catalyst EA having a $Na_2O$ concentration of 50 ppm. In both runs depicted in FIG. 5, steam cofeed in an amount of 1 wt. % based upon the benzene feed was employed, similarly as described above with respect to the earlier experimental work. In Run 5 (FIG. 3) the water was boiler condensate having a pH of about 8.4 and in all of the other runs, the steam cofeed was derived from ionized water.

Having described specific embodiments of the present invention, it will be understood that modification thereof may be suggested to those skilled in the art, and it is intended to cover all such modifications as fall within the scope of the appended claims.

What is claimed is:

1. In a process for the alkylation of aromatic compounds, the steps comprising:
   (a) supplying a feedstock containing an aromatic substrate into a reaction zone and into contact with a shape selective crystalline silica polymorph silicalite alkylation catalyst having a sodium content of less than 100 ppm expressed as $Na_2O$;
   (b) supplying an alkylating agent to said reaction zone;
   (c) operating said reaction zone at temperature and pressure conditions to effect alkylation of said aromatic substrate by said alkylating agent; and
   (d) recovering alkylated aromatic substrate from said reaction zone.

2. The method of claim 1 further comprising the step of cofeeding water to said reaction zone in an amount of at least 1 wt. % based upon said aromatic substrate.

3. The method of claim 1 wherein the sodium content of said silicalite catalyst is no greater than 50 ppm expressed as $Na_2O$.

4. The method of claim 1 wherein the sodium content of said silicalite catalyst is no more than 30 ppm expressed as $Na_2O$.

5. The method of claim 1 wherein the sodium content of said silicalite catalyst is no greater than 20 ppm expressed as $Na_2O$.

6. The method of claim 1 wherein said aromatic substrate comprises benzene or toluene and said alkylating agent contains one or two carbon atoms.

7. The method of claim 6 wherein said alkylating agent is ethylene.

8. The method of claim 1 wherein said aromatic substrate comprises benzene.

9. The method of claim 8 wherein said alkylating agent is ethylene.

10. The method of claim 9 wherein the sodium content of said silicalite catalyst is no greater than 50 ppm expressed as $Na_2O$.

11. The method of claim 9 wherein the sodium content of said silicalite catalyst is no more than 30 ppm expressed as $Na_2O$

* * * * *